United States Patent [19]

Skållen et al.

[11] Patent Number: 4,635,470
[45] Date of Patent: Jan. 13, 1987

[54] APPARATUS AND METHOD FOR PERMEABILITY MEASUREMENT

[75] Inventors: Bengt Skållen, Säffle; Kjell Ljungkvist, Gothenburg; Urban Gren, Mölndal, all of Sweden

[73] Assignee: Eur-Control Kalle AB, Sweden

[21] Appl. No.: 694,389

[22] PCT Filed: May 11, 1984

[86] PCT No.: PCT/SE84/00177

§ 371 Date: Jan. 7, 1985

§ 102(e) Date: Jan. 7, 1985

[87] PCT Pub. No.: WO84/04591

PCT Pub. Date: Nov. 22, 1984

[30] Foreign Application Priority Data

May 11, 1983 [SE] Sweden ............... 8302719

[51] Int. Cl.$^4$ .............................. G01N 11/06
[52] U.S. Cl. ..................... 73/63; 73/863.83; 162/263
[58] Field of Search ............. 73/63, 863.83, 863.84, 73/863.85, 863.86; 162/263, 49

[56] References Cited

U.S. PATENT DOCUMENTS

| | | | |
|---|---|---|---|
| 1,966,712 | 7/1934 | Fisher et al. | 73/863.54 |
| 1,970,521 | 8/1934 | Harvey | 73/63 |
| 3,847,022 | 11/1974 | McGinnis | 73/863.83 |
| 3,949,614 | 4/1976 | Abonnenc | 73/863.83 |
| 4,114,427 | 9/1978 | Iguchi et al. | 73/63 |
| 4,262,533 | 4/1981 | Jaeger | 73/863.83 |
| 4,269,064 | 5/1981 | Johnson et al. | 73/863.84 |
| 4,475,410 | 10/1984 | Jaeger | 73/863.84 |

FOREIGN PATENT DOCUMENTS 384269 of 1976 Sweden .
417645 3/1981 Sweden .

*Primary Examiner*—Stewart J. Levy
*Assistant Examiner*—Hezron E. Williams
*Attorney, Agent, or Firm*—Ostrolenk, Faber, Gerb & Soffen

[57] ABSTRACT

The invention relates to an apparatus and a method for determining the drainability by permeability measurements. The apparatus is provided for taking a sample of a suspension, particularly a fibre suspension, e.g. such as flows in a pipe (2), said apparatus including a sampling piston housing (4) connected to the pipe (2) and accommodating a sampling piston (5) which can be displaced into the pipe (2) and has a through hole for forming a sample chamber (9) for taking out a pulp sample. The housing (4) is in communication with a dilution and mixing chamber (35) including an agitation or mixing device (36), the lower portion of the chamber (35) being closed off by an end member (23) with a screening plate (22). In the method in accordance with the invention there first takes place measurement on the entire pulp sample, subsequent to which the sample is liberated from its fine fraction by a washing process in the mixing chamber (35), measurement on the proportion of fibre in the pulp sample then taking place, for which purpose the permeability of the pulp bed formed against the screening plate (22) is measured during one or more pressure drops, possibly with intermediate slushing with the aid of the mixing device (36) and reformation of the pulp bed.

10 Claims, 1 Drawing Figure

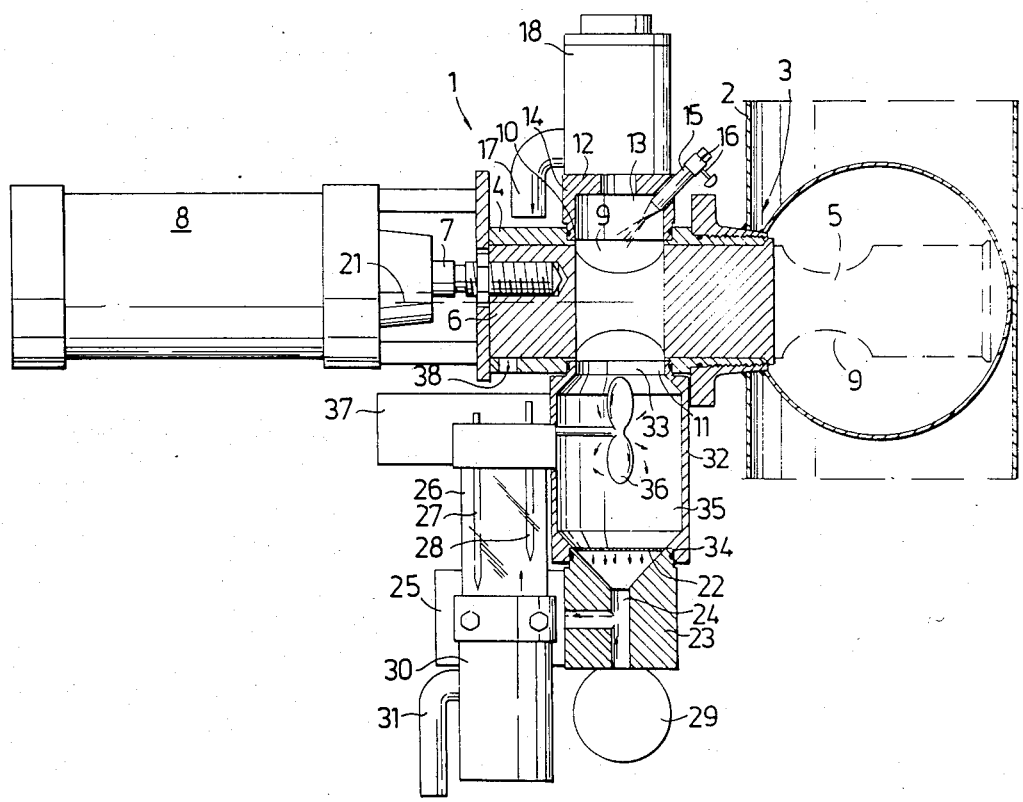

APPARATUS AND METHOD FOR PERMEABILITY MEASUREMENT

The present invention relates to an apparatus and a method for permeability measurement, said apparatus is provided for sampling a suspension passing through a pipe, particularly a fibrous suspension, and comprises a sampling cylinder housing attachable round an opening made in the wall of the pipe, the housing being open towards the interior of the pipe and accommodating concentrically an axially displaceable sampling cylinder, adapted for taking a suspension sample from the pipe for the purpose of determining its permeability or freeness level and also the permeability of a sample impoverished of fines or smaller fibre fragments.

Drainage transmitters or meters provided so far usually have a very complicated structure, which results in expensive service, as well as the installation of these meters in a pulp line requiring special arrangements. Due to this the weight of this type of meter rarely falls below 50 kg, which makes dismantling the meter more difficult when it is to be cleaned, for example. Other problems with this kind of meter is that they are easily blocked up by fibers remaining from the fiber suspension after sampling. These meters moreover lack the possibility of determining the permeability of the long fiber portion of the pulp sample.

The present invention has the object of providing a drainage rate transmitter of the kind mentioned in the introduction, which is substantially distinguished in that the sampling piston has a cylindrically formed through-hole at right angles to its longitudinal direction, the hole forming a sample chamber, such that when the sampling piston is in its retracted position inside the housing the chamber is in register with at least one hole of substantially the same diameter in the cylindrical surface of the housing, for connecting to it a preferably cylindrical casing defining a mixing and dilution chamber, in which there is an agitating or mixing device, the casing being provided with two opposing openings, of which one has the same diameter as the hole in the cylindrical surface of the housing and the other has a shape affording sealing connection to an end wall member carrying a screening plate, said member being provided with a drainage collection duct under the screening plate for conveying measuring water passing through a fibre bed formed on the screening plate to measuring means for determining the drainage properties of the sample taken, and also of a sample which has been completely or partially liberated from smaller fibre fragments by a special separation method. By the sample-taking chamber being arranged in line with the spaces required for achieving a homogenous pulp bed from a suspension sample there is obtained according to the invention better formation or growth of the pulp on the screening plate, as well as complete flushing after each sampling procedure, since there are no dead spaces where the remains of previous samples can catch and negatively affect the measuring result. The simple construction means that no heavy details need to be removed for inspecting the screen and neither are any tools required, since the cylindrical wall and the end wall member carrying the screening plate with the intermediate mixing chamber may be fastened to the housing with the aid of toggle catches.

The present invention also relates to a method of determining the permeability, particularly in a fibre suspension, the method being substantially distinguished in that smaller fibre fragments in a pulp sample introduced into the measuring or mixing chamber, after filtering against the screening plate and subsequent permeation of water during one or more pressure drops, possibly after slushing by agitation of the pulp bed built up against the screening plate between the different measurements, are removed by once again bringing the pulp bed into suspension by slushing with the aid of the mixing or agitating means and a simultaneously applied flow of water, after which the fibre suspension, substantially impoverished of fine material, is once again filtered against the screening plate after terminated agitation, the permeability of the pulp bed formed once again being measured during one or more pressure drops, possibly with intermediate slushing and reformation of the bed.

The invention is described in detail below with reference to the appended drawing, which illustrates an axial section through a preferred embodiment of a drainage rate transmitter in accordance with the present invention.

The drainage rate transmitter 1 illustrated on the drawing includes a cylindrical sampling piston housing 4, fixable to an opening 3 made in a pipe 2 or a vessel with agitated contents. The housing 4 concentrically accommodates a sampling position and a retracted position with the aid of a piston rod means 7 attached to its outer end portion 6, the piston rod being associated with a pneumatic cylinder 8. There is a sample chamber 9 in the piston 5 in the form of a through-hole transverse the longitudinal direction of the piston 5, and when the piston is in its retracted position inside the housing 4 the chamber 9 forms part of a measuring space and has its axis coinciding with those of two holes 10 and 11 in the cylindrical surface of the housing 4. As with the sample chamber 9 these holes are also preferably cylindrically formed and of the same diameter as the chamber 9. The upper hole 10 continues into a space 13 defined by a cylindrical wall 14 of the same diameter as the hole 10 and by an end wall 12. The space 13, hole 10, sample chamber 9 and hole 11 thus form a continuous chamber, such as to avoid dead spaces which can give rise to collections of fibres from different samplings. A measuring water nozzle 15 opens out into the space 13, and the nozzle is in communication with a water supply via a valve 16. The space 13 is in a communication with an outlet 17 via a hole in the end wall 12, this communication being regulated by an outlet valve 18.

For eliminating rotation of the sampling piston 5 in relation to the housing 4, the piston rod 7 may be exchanged for two mutually parallel partial piston rods, or attached, as illustrated on the drawing, to the outward end portion 6 of the piston 5 at a point situated at a distance from the axis of the piston 5.

The drainage rate transmitter in accordance with the present invention is suitably used for sampling suspensions which have a concentration of about 1–10%, and for the cases where the permeability of a sample, liberated from smaller fibre fragments is to be determined. The lower hole 11 of the housing 4 opens out into a mixing and dilution chamber 35 formed by a casing 32 which has two opposing openings 33, 34, of which the upper 33 fits sealingly into the hole 11 and the lower 34 is adapted to seal against an end member 23 carrying a screening plate 22. The end member 23 includes a drainage collecting duct 24 arranged under the screening plate 22, the duct opening out conically in the area under the screening plate. Via a dewatering valve 25 the duct 24 is in communication with a measuring glass 26 containing two electrodes 27, 28, and in an area directly under its conical portion is connected to a flushing water supply via a valve 29. The measuring glass 26 may be emptied via an outlet 31 and an outflow control valve 30. Depending on the pulp concentration, the length of the casing 32 may be varied with a variation in the volume of the mixing chamber as a result. Dilution of the suspension sample may be carried out to give it a suitable concentration level with the aid of the variation in volume of the mixing chamber 35 between the housing 4 and end member 23. The intention with the dilution is to arrive at a concentration level in the sample where the pulp flocking properties are reduced, and also to facilitate separation of smaller fibre fragments. With higher concentrations the pulp sample is usually heavily flocked, which affects the measurement procedure, since waterways are formed between the flocks, causing the measuring water to flow in the waterways between the flocks and in turn cause an unsteady output signal, which may give a faulty measuring result. The measuring result is considerably improved when the pulp is diluted down to about 0.8% or lower, with the aid of a mixing and dilution chamber of appropriate volume. For mixing during the dilution of the sample to the desired concentration and also for achieving sufficient turbulence for taking away the fine fraction there is a mixing or agitating propeller 36 in the mixing chamber 35, the propeller being driven by a motor 37. The revolutionary speed of the motor and the implementation of the propeller 36 are such that during the simultaneous introduction of measuring water at a suitable pressure such large shearing forces may be achieved at the screening plate 22 that a pulp plug is not formed. Short fibre fragments can thus be separated by passing through the perforations in the screening plate 22.

It is desirable, inter alia for cleaning purposes, quickly and easily to remove the upper end wall 12, casing 32 and end member 23 with the screening plate 22. This is enabled with the end of suitably placed, unillustrated toggle catches.

The measuring prodedure in accordance with the present invention and using the equipment described hereinbefore, when the suspension sample has a pulp concentration of about 1–10%, or when measurement of the drainability properties of the entire pulp as well as those of the long fibre content takes place, is performed in the following manner:

A. Sampling

The pneumatic cylinder 8 is activated so that the sampling piston 5 is thrust into the pipe 2 simultaneously as the outflow control valve 30 under the measuring glass 26 and outlet valve 18 are open and the flushing water valve 29, measuring water valve 16 and dewatering valve 25 under the screening plate 22 are closed. This means that the mixing chamber 35, which also serves as a measure chamber, is filled with water to the bottom edge of the piston 5. Superfluous water runs out through a vent 38 in the outer end portion of the housing 4. When sampling is finished, the piston 5 has been completely retracted into its retracted position and mixing begins.

B. Mixing

All the valves have the same operational status as under A. The sample taken out of the pipe 2 with the aid of the piston 5 is mixed with the water in the mixing chamber 35 with the aid of the propeller 36. Mixing conditions may vary depending on the pulp concentration, as mentioned previously. The intention with dilution is to obtain a concentration level in which the flocking properties of the pulp are heavily reduced, which is the case when the concentration is at about 0.8% or less.

C. Predrainage

The outlet valve 18 is closed and the measuring water valve 16 and the dewatering valve 25 under the screening plate 22 are opened. The outflow control valve 30 under the measuring glass 26 is still open and the flushing water valve 29 still closed. This means that during draining, which takes place in the mixing chamber 35, the fibres in the suspension are deposited on the screening plate 22 to form a pulp bed, with the aid of the measuring water. The drained water goes through the pulp on the screening plate 22 via the outflow control valve 30 under the measuring glass and out through the outlet 31.

D. Measuring

Excepting the outflow control valve 30 under the measuring glass 26, all the valves have the same operational status as under C. The outflow control valve 30 is now closed. This means that the drainage which passes through the pulp on the screening plate 22 is collected in the measuring glass 26, where the rising time between the electrodes 27, 28 is measured for determining the permeability and/or the freeness level in the sample. This measurement can be repeated at one or more different pressures, with possible intermediate slushing.

E. Slushing

All valves are closed. The propeller 36 is activated and the fibre bed formed is slushed up again.

F. Washing

The smaller fibre fragments and fine material are separated by the valves being put into the operational state as in item C while the propeller 36 is still activated. There are thus obtained sufficiently large shearing forces to prevent the formation of a fibre bed. The perforations in the screening plate 22 therefore allow passage of fine material, which is thus removed from the sample.

G. Measurement

Measurement according to item D is carried out on the sample impoverished of fine material. When the measuring result has been registered the pressure can be varied, if so required, and a new measurement carried out at a different pressure. This measurement can be carried out with or without an intermediate slushing according to item E. The measuring values now obtained are subsequently compared with the measuring value or values obtained according to item D to determine the content of fine fraction in the pulp suspension.

H. Flushing

The flushing water valve 29 and the outlet valve 18 are opened. Simultaneous with closing the measuring water valve 16 and the dewatering valve 25 under the screening plate 22, while the outflow control valve 30 under the measuring glass 26 is open so that the measuring water in the measuring glass 26 can be tapped off. When flushing is terminated, the flushing water valve 29 is closed and the water remaining in the chamber 35 is used to dilute the next sample. A new sample can now be taken.

What is claimed is:

1. An apparatus for sampling a fibrous suspension and for measuring permeability values of the suspension, the apparatus comprising:

a cylindrical sampling piston housing attachable to a pipe carrying the suspension, at an opening in a wall of the pipe, a concentrically disposed and axially displaceable sampling piston adapted for retrieving a suspension sample from the pipe, the sampling piston having a cylindrically shaped through hole extending at a right angle to a longitudinal direction of the piston, the hole forming a sample chamber which is so disposed that when the sampling piston is in a retracted position inside the housing, the sample chamber is in register with at least one hole, of substantially the same diameter, in a cylindrical surface of the housing, the hole which forms the sample chamber being defined around a longitudinal axis;

a cylindrical casing defining a mixing and dilution chamber and a mixing device disposed in the mixing and dilution chamber, the casing having two opposing openings, of which one of the openings has the same diameter as the hole in the cylindrical surface of the housing and is in register with the hole in the cylindrical surface of the housing;

an end wall member and a screening plate located in an opening in the end wall member, the opening of the end wall member being sealingly connected to the other opening in the casing which is located away from the sampling piston, the mixing and dilution chamber being defined around a respective longitudinal axis which respective axis is coaxially aligned with the axis of the sample chamber;

a drainage collection duct disposed on the side of the screening plate which faces away from the mixing and dilution chamber and a source of pressurized liquid disposed on the side of the screening plate which is away from the mixing and dilution chamber, the source of pressurized liquid being adapted to provide a stream of flushing liquid which flows through the screening plate into the mixing and dilution chamber and then into the sample chamber generally in a direction along the longitudinal axes of the sample chamber and the mixing and dilution chamber whereby substantially all of the fibrous suspension will be evacuated whenever the source of pressurized liquid is operated in consequence of the alignment of the sample chamber and the mixing and dilution chamber and avoidance of circuitous routes for the flushing liquid.

2. Apparatus as claimed in claim 1, characterized in that the cylindrical surface of the housing (4) is provided with two mutually opposing holes (10, 11) in register with the chamber in the piston (5), the upper hole (10) merging into a space (13) defined by an end wall (12) integral with a cylinder wall (14) which is sealingly fixable over the hole (10), in that an inlet (15) for the supply of measuring water and washing water opens out into the space (13), and in that a flushing water outlet (17), which can be put in communication with the space (13) via a hole in the end wall (12), is arranged in the area adjacent the end wall.

3. Apparatus as claimed in claim 1, characterized in that the movement in the housing (4) of the sampling piston (5) is provided with the aid of a pneumatic cylinder (8), the piston rod (7) of which is attached to the outward end portion (6) of the sampling piston (5) at a point spaced from the axis (21) of the piston (5).

4. Apparatus as claimed in claim 3, characterized in that the agitating or mixing device arranged in the mixing chamber (35) consists of a motor-driven propeller (36) situated centrally inside the mixing chamber (35) with its axis of rotation horizontal or transverse to the longitudinal direction of the mixing chamber (35).

5. Apparatus as claimed in claim 4, characterized in that the end wall (12) with its cylindrical wall (14) and the end member (23) with the intermediate mixing chamber casing (32) are removably fixable to the cylindrical surface of the housing (4) with the aid of toggle catches.

6. An apparatus for sampling a fibrous suspension which flows through a pipe and for measuring permeability values of the suspension both before and after a fine fraction content of the suspension has been removed therefrom, the apparatus comprising:

a cylindrical sampling piston housing attachable to the pipe carrying the suspension, at an opening in a wall of the pipe, a concentrically disposed and axially displaceable sampling piston adapted for retrieving a suspension sample from the pipe, the sampling piston having a cylindrically formed through hole extending at a right angle to a longitudinal direction of the piston, the hole forming a sample chamber which is so disposed that when the sampling piston is in a retracted position inside the housing, the sample chamber is in register with at least one hole of substantially the same diameter in a cylindrical surface of the housing, the hole which forms the sample chamber being defined around a longitudinal axis;

a cylindrical casing defining a mixing and dilution chamber and a mixing device disposed in the mixing and dilution chamber, the casing having two opposing openings, of which one has the same diameter as the hole in the cylindrical surface of the housing and is in register with the hole in the cylindrical surface of the housing;

an end wall member and a screening plate located in an opening in the end wall member, the opening of the end wall member being sealingly connected to the other opening in the casing which is located away from the sampling piston, the mixing and dilution chamber being defined around a longitudinal axis of the mixing and dilution chamber which axis is coaxially aligned with the axis of the hole in the sample chamber;

a drainage collection duct disposed on a side of the screening plate which faces away from the mixing and dilution chamber and a source of pressurized liquid disposed on the side of the screening plate which is away from the mixing and dilution chamber and adapted to provide a stream of flushing liquid which flows through the screening plate into the hole of the sampling piston and generally in a direction along the longitudinal axes of the sampling piston and the mixing and dilution chamber whereby substantially all of the fibrous suspension will be evacuated whenever the source of pressurized liquid is operated in consequence of the alignment of the sample chamber and the mixing and dilution chamber;

means for agitating the suspension sample and simultaneously passing a liquid through the sample chamber and through the mixing and dilution chamber in a manner that the fine fraction content flows through the screening plate while long fibres in the suspension remain and form a pulp bed of long fibres on the screening plate;

means for causing water to flow through the bed of long fibres located on the screening plate and for measuring the quantity of the water that passes therethrough in a predetermined time to determine the permeability of the bed of long fibres.

7. An apparatus for measuring the permeability of a fibrous suspension located in a vessel, the apparatus comprising:
a piston-based sampling arrangement adapted for retrieving a sample of the fibrous suspension from the vessel and a mixing and dilution chamber wherein the sample is introduced, mixed and measured;
the piston-based arrangement including:
a housing having an axial dimension and a first opening at an axial end of the housing, the axial end of the housing being adapted to be sealingly mounted to the vessel at an opening in the vessel;
a piston reciprocatingly movable in the housing, a portion of the piston being movable into and out of the housing through the first opening in the housing;
a through hole extending through the portion of the piston, generally transversely to the axial dimension of the housing, the through hole being intended to be filled with the sample of fibrous suspension; and
a second opening in the housing, the second opening being defined around a transverse axis which extends transversely to the axial dimension of the housing;
the mixing and dilution chamber including:
a casing defining the mixing and dilution chamber, the casing having a respective axis and an axial opening, the casing being mounted to the housing so that the mixing and dilution chamber is in communication with the interior of the housing and so that the axis of the casing is coaxial with the transverse axis;
the mixing and dilution chamber and the through hole in the piston being so disposed that when the piston is in a retracted position, the through hole, the second opening in the housing, and the mixing and dilution chamber are all in registration with one another and are lined up along the transverse axis;
a mixing device disposed in the mixing and dilution chamber;
a screening plate disposed in the casing axially opposite to the axial opening;
flushing means disposed on a side of the screening plate facing away from the axial end, the flushing means being adapted for introducing a flushing column of liquid through the mixing chamber and the through hole which flushing, liquid is directed to travel along the transverse axis to assure effective and substantially complete flushing of all of the sample fibrous suspension from both the mixing and dilution chamber and the through hole in the cylinder at the end of a measurement cycle.

8. Method based on permeability measurements for determining the drainage properties of a suspension, flowing through a conduit such as a pipe (2), particularly a fibre suspension, with the aid of a drainage rate transmitter including a sampling piston housing (4) attachable round an opening (3) made in the wall of the pipe (2), the housing being open towards the interior of the pipe (2) and accommodating concentrically an axially displaceable sampling piston (5), adapted for taking out a suspension sample, said piston (5) having a cylindrically formed through hole at right angles to its longitudinal direction, the hole forming a sample chamber (9), such that when the sampling piston (5) is in its retracted position inside the housing (4) the chamber (9) is in register with at least one hole (11) of substantially the same diameter in a cylindrical surface of the housing (4), for connecting to it a preferably two opposing openings (33, 34), of which one has the same diameter as the hole (11) in the cylindrical surface of the housing (4) and the other has a shape affording the sealing connection of a screening plate (22), from which measuring water is transported to following measuring means (26–28) for determining permeability of the sample, characterized in that a pulp sample is taken from the fibre suspension flowing in the pipe (2), and diluted with a given volume of water as the sample is introduced into a dilution and mixing chamber (35), with mixing being carried out with the aid of the agitation device (36); that after a predetermined time the agitation is terminated and a pulp bed is formed on the screening plate (22) with the aid of preferably pressure controlled measuring water; that the permeability of the sample being determined with the aid of the wholly or partially ready-formed pulp bed by a given quantity of water being allowed to pass through the bed and through the screening plate (22) at one or more pressure drops, possibly with intermediate slushing-up and reformation of the bed, the water being taken from under the plate to following measuring means (26–28) for determining a first measurement value; that subsequent thereto the pulp bed is once again slushed up from the screening plate (22) into suspension with the aid of an agitation by the mixing device (36), whereupon a flow of water is added and smaller fibre fragments thus being separated from the sample to pass through the screening plate; that the sample depleted of fine fraction is reformed again against the screening plate (22) after terminated washing, the permeability of the pulp bed on the screening plate (22) then being measured during one or more pressure drops, possible with intermediate slushing and reformation, for determining a second measurement value; and that both the values obtained are subsequently compared for determining not only the permeability of the pulp suspension but also the quantity of fine fraction in the pulp suspension.

9. A method for determining the degree of permeability and the fine fraction content of a fibrous suspension flowing through a conduit such as a pipe with an apparatus including a sampling piston housing attachable to an opening in a wall of the pipe, the piston housing accommodating a concentrically disposed and axially displaceable sampling piston adapted for retrieving a suspension sample from the pipe, the piston having a cylindrically shaped through hole extending at a right angle to a longitudinal direction of the piston, the hole defining a sample chamber which is so oriented that when the sampling piston is in a retracted position inside the housing, the sample chamber is in register with at least one hole of substantially the same diameter in a cylindrical surface of the housing, the apparatus further having a casing abutting the housing and defining a mixing and dilution chamber with an opening than can communicate into the sample chamber and further including a mixing device in the dilution chamber, the sample chamber and the dilution chamber being defined around a respective longitudinal axis thereof, with the axes being substantially coaxially disposed relative to each other when the sampling piston is in its retracted position in a manner that a continuous chamber comprised of the dilution chamber and the sample chamber is formed, the continuous chamber having internally aligned surfaces which promote flushing of the fibrous suspension from both chambers whenever required; the apparatus further including a screening plate which is centered about the longitudinal axis of the mixing chamber at an end wall thereof which is located oppositely to opening in the casing; the method comprising the steps of:

introducing a quantity of dilution liquid into the mixing and dilution chamber;

retrieving the suspension sample from the conduit and bringing the sample chamber in the piston into registration with the mixing and dilution chamber to intermix the suspension sample with the dilution liquid;

operating the mixing device and simultaneously passing a liquid through the sample chamber and through the mixing and dilution chamber in a manner that causes the fine fraction content of the suspension to be filtered out from the sampling chamber and from the mixing and dilution chamber to retain substantially only a long fiber content of the fibrous suspension;

measuring the degree permeability of the suspension sample from which the fine fraction content has been removed; and directing flushing liquid through the sample chamber and the mixing and dilution chamber, the flushing liquid flowing along the longitudinal axis of the chambers whereby in consequence of the alignment of the sampling chamber and the mixing and dilution chamber and the flow of the flushing liquid along the axes of the chambers, the chambers are effectively purged of all of the suspension sample and are in a condition for receiving a subsequent suspension sample from the conduit.

10. Method as claimed in claim 9, characterized in that the permeability of the pulp bed is measured during a formation phase during the build-up of the pulp bed on the screening plate (22).

* * * * *